United States Patent
Ueno et al.

(10) Patent No.: US 6,414,195 B1
(45) Date of Patent: Jul. 2, 2002

(54) METHOD OF PRODUCING FORMALDEHYDE DIRECTLY FROM METHANE

(75) Inventors: Akifumi Ueno, Tenryu; Naoto Azuma, Hamamatsu; Tomomi Sugino, Shimizu; Ayako Kido, Fuji, all of (JP)

(73) Assignee: President of Shizuoka University, Shizuoka (JP)

( * ) Notice: Subject to any disclaimer, the term of this patent is extended or adjusted under 35 U.S.C. 154(b) by 0 days.

(21) Appl. No.: 09/576,293

(22) Filed: May 23, 2000

(30) Foreign Application Priority Data

Mar. 27, 2000 (JP) ........................................ 2000-087641

(51) Int. Cl.$^7$ .............................................. C07C 45/28

(52) U.S. Cl. ...................... 568/482; 568/449; 568/470; 568/493

(58) Field of Search ................................ 568/449, 470, 568/475, 482, 491, 492, 493; 502/255, 171; 423/335

(56) References Cited

U.S. PATENT DOCUMENTS

| 4,705,771 A | 11/1987 | Spencer ...................... 502/255 |
| 5,300,703 A | 4/1994 | Knifton ...................... 568/794 |
| 6,294,701 B1 * | 9/2001 | Ueno et al. .................. 568/482 |

FOREIGN PATENT DOCUMENTS

| EP | 0 419 077 | 3/1991 |
| EP | 1 038 578 A 2 | 9/2000 |
| WO | WO 86/06063 | 10/1986 |
| WO | WO 95/13869 | 5/1995 |

OTHER PUBLICATIONS

Hangchun Hu, et al., "Surface Structures of Supported Molybdenum Oxide Catalysts: Characterization by Raman and MO $L_3$–Edge Xanes," Journal of Physical Chemistry, 95, 1995, pp. 10897–10910.

Claude Rocchiccioli–Deltcheff, et al., "Structure and Catalytic Properties of Silica–Supported Polyoxomolybdates," Journal of Catalysis, 126, 1990, pp. 591–599.

J.B. Moffat, et al., "The Oxidation of Methane on Heteropolyoxometalates," Journal of Catalysis, 109, 1988, pp. 206–211.

S. Kasztelan, et al., "The Oxidation of Methane on Heteropolyoxometalates," Journal of Catalysis, 112, 1988, pp. 54–65..

Chemical Abstracts, vol. 128, AN 61300, 1997.
Chemical Abstracts, vol. 126, AN 48569, 1996.
Chemical Abstracts, vol. 126, AN 77111, 1995.
Chemical Abstracts, vol. 123, AN 209732, 1995.
Chemical Abstracts, vol. 118, AN 46556, 1992.
Chemical Abstracts, vol. 117, AN 236244, 1992.
Chemical Abstracts, vol. 108, AN 204092, 1987.
Derwent Abstracts, AN 95–355203/46, JP 07 242578, Sep. 19, 1995.
Derwent Abstracts, AN 80–80026, JP 55 125119, Sep. 26, 1980.

* cited by examiner

Primary Examiner—Sreeni Padmanabhan
(74) Attorney, Agent, or Firm—Oblon, Spivak, McClelland, Maier & Neustadt, P.C.

(57) ABSTRACT

The present invention provides a method of using a silica-supported 12-molybdosilicic acid catalyst consisting of 12-moloybdosilicic acid supported on silica, in which 12-molybdosilicic acid is supported in an amount not smaller than 10 mass % on silica, wherein the reaction system is heated in the presence of the silica-supported 12-molybdosilicic acid catalyst to the operating temperature of the catalyst at a rate not lower than 100° C./min.

12 Claims, 7 Drawing Sheets

F I G. 1

F I G. 2

FIG. 3 a: THERMAL DECOMPOSITION WITHIN AIR b: WATER VAPOR TREATMENT AFTER THERMAL DECOMPOSITION WITHIN AIR AT 600°C, FOLLOWED BY THERMAL DECOMPOSITION AGAIN

○ : FORMALDEHYDE   ⊘ : CO
● : $CO_2$          □ : METHAN

FIG. 11C

METHOD OF PRODUCING FORMALDEHYDE DIRECTLY FROM METHANE

CROSS-REFERENCE TO RELATED APPLICATIONS

This application is based upon and claims the benefit of priority from the prior Japanese Patent Application No. 2000-087641, filed Mar. 27, 2000, the entire contents of which are incorporated herein by reference.

BACKGROUND OF THE INVENTION

The present invention relates to a method of producing formaldehyde, particularly to a novel catalyst that permits producing formaldehyde directly from methane at a high yield and a method of producing formaldehyde by using the novel catalyst.

Formaldehyde is produced by partial oxidation reaction of methanol. Half the methanol produced in an amount of one million tons in a year in Japan is used as a raw material for the production of formaldehyde. The produced formaldehyde is used as a raw material of synthetic resins such as phenolic resins and urea resins or as a raw material of various medicines.

Methanol is synthesized from hydrogen and carbon monoxide obtained by water vapor reforming reaction of methane. The conventional process of producing formaldehyde is as given below:

Methane→$H_2$/CO→Methanol→Formaldehyde

The reaction for preparing $H_2$/CO from methane is an endothermic reaction using a large amount of high temperature water vapor, which is one of typical processes consuming a large amount of energy. On the other hand, the reaction for synthesizing methanol from $H_2$/CO is an exothermic reaction. In order to prevent the reaction heat from being generated excessively, the CO conversion rate must be suppressed to about 10% in operating the process unit. Also, the conversion rate of methanol must be suppressed in operating the process unit in the production of formaldehyde by partial oxidation of methanol in order to suppress formation of carbon dioxide and carbon monoxide. In short, the conventional process of producing formaldehyde is a process consuming a large amount of energy and requiring a very complex operation of the process unit.

In order to avoid the large energy-consuming process in the production of formaldehyde, it is necessary to develop a new producing process that permits producing formaldehyde without involving the step of water vapor reformation of methane to produce $H_2$/CO.

It is considered theoretically possible to produce methanol and formaldehyde by partial oxidation of methane, i.e., direct synthesis from methane, as suggested by chemical reaction formulas given below:

$CH_4+1/2O_2 \rightarrow CH_3OH$, $CH_4+O_2 \rightarrow HCHO+H_2O$

Therefore, vigorous researches are being made over more than these 50 years on the method of directly synthesizing methanol or formaldehyde from methane in research institutes over the world. Since a catalyst is required for the reactions given above, the major portion of these researches has been concentrated on the development of an effective catalyst. For example, catalysts having molybdenum oxide, vanadium oxide, chromium oxide, etc. supported by silica are reported in, for example, "Chemistry Letter, 1997, p31–32" and "Catalyst Today, 45, p29–33(1998)".

However, the yield of methanol or formaldehyde is very low, i.e., less than 1% in general, even in the presence of these catalysts. It is said among the researchers in this field that it is difficult for the yield of methanol or formaldehyde to exceed 4%. In other words, the yield of 4% is said to be a wall that cannot be broken in the direct synthesis of methanol or formaldehyde from methane. Further, the methane conversion rate of at least 10% is required for putting the process to practical use. In conclusion, a process for direct conversion from methane into formaldehyde with a practical yield of formaldehyde has not yet been developed.

BRIEF SUMMARY OF THE INVENTION

An object of the present invention is to produce formaldehyde with a high yield directly from methane by a process that does not involve a water vapor reforming step of methane, which is a step consuming a large amount of energy, and that does not bring about an air pollution or water contamination problem. To achieve the object, the present invention provides a novel catalyst and a method of producing formaldehyde by using the novel catalyst.

The present inventors have conducted an extensive research on a catalyst excellent in its activity of partially oxidizing methane and on the conditions of the reaction carried out in the presence of the particular catalyst, and found that a silica-supported 12-molybdosilicic acid catalyst, in which 12-molybdosilicic acid is supported on silica, is excellent in its activity of partially oxidizing methane and, thus, is very effective when used as a catalyst in the synthesis of formaldehyde directly from methane.

12-molybdosilicic acid (which may be hereinafter referred to as SMA in some cases) is poor in thermal stability. Therefore, in using the novel catalyst, it was required to carry out the synthetic reaction of formaldehyde while suppressing the thermal decomposition of the SMA catalyst. The present inventors have continued an extensive research bearing this in mind to arrive at a very important finding. Specifically, it has been found that, for suppressing the thermal decomposition of the SMA catalyst, it is effective to carry out the synthetic reaction of formaldehyde in the presence of the particular catalyst under a water vapor atmosphere. It has also been found that it is very important to control appropriately the temperature elevation rate in heating the reaction system to the reaction temperature.

The present invention, which has been achieved on the basis of the finding given above, is featured as follows:

(1) A method of using a silica-supported 12-molybdosilicic acid catalyst consisting of 12-molybdosilicic acid supported on silica, in which 12-molybdosilicic acid is supported in an amount not smaller than 10 mass % on silica, wherein the reaction system is heated in the presence of the silica-supported 12-molybdosilicic acid catalyst to the operating temperature of the catalyst at a rate not lower than 100° C./min.

(2) A method of using a silica-supported 12-molybdosilicic acid catalyst consisting of 12-molybdosilicic acid supported on silica, in which 12-molybdosilicic acid is supported in an amount not smaller than 10 mass % on silica having a specific surface area not smaller than 500 $m^2$/g, wherein the reaction system is heated in the presence of the silica-supported 12-molybdosilicic acid catalyst to the operating temperature of the catalyst at a rate not lower than 100° C./min.

(3) A method of producing formaldehyde directly from a mixed gas of methane and oxygen in the presence of a silica-supported 12-molybdosilicic acid catalyst consisting of 12-molybdosilicic acid supported on silica, in which 12-molybdosilicic acid is supported in an amount not smaller than 10 mass % on silica, wherein the reaction system is heated in the presence of the silica-supported 12-molybdosilicic acid catalyst to the operating temperature of the catalyst at a rate not lower than 100° C./min.

(4) The method of producing formaldehyde according to item (3), wherein the volume ratio of methane/oxygen in the mixed gas falls within a range of between 9/1 and 4/6, and the reaction temperature in the presence of the catalyst falls within a range of between 550° C. and 650° C.

(5) The method of producing formaldehyde according to item (3), wherein a water vapor is added to the mixed gas of methane and oxygen in an amount of 40 to 80% by volume based on the total reaction gas consisting of the mixed gas and the water vapor.

(6) The method of producing formaldehyde according to item (4), wherein a water vapor is added to the mixed gas of methane and oxygen in an amount of 40 to 80% by volume based on the total reaction gas consisting of the mixed gas and the water vapor.

According to the present invention, formaldehyde can be synthesized directly from methane with a high yield exceeding 15%, which suggests a breakaway from the conventional process consuming a large amount of energy. It follows that the present invention is expected to make a great contribution to the energy saving in the chemical industries.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

In the present invention, reaction between methane and oxygen is carried out in the presence of a catalyst for producing formaldehyde directly from methane. The catalyst used in the present invention is prepared by having 12-molybdosilicic acid supported on a silica carrier.

The silica-supported 12-molybdosilicic acid catalyst of the present invention can be prepared by an impregnation method as follows. Specifically, 12-molybdosilicic acid (SMA) is sufficiently dissolved in pure water at room temperature. Then, a silica powder is dipped in the solution, followed by evaporating the water such that the catalyst is not dried completely. If the catalyst is completely dried and heated at 350° C. or more, SMA within the catalyst is thermally decomposed into silica and molybdenum oxide, as shown below:

$$H_4SiMo_{12}O_{40} \rightarrow SiO_2 + 12MoO_3 + 2H_2O$$

Therefore, the water should be evaporated on, preferably, a water bath while heating and stirring the solution such that the catalyst is not dried completely.

After the water evaporation, the catalyst is further dried for obtaining the catalyst of the present invention.

SMA used as a raw material is a compound having a molecular formula of $H_4SiMo_{12}O_{40}$. In the present invention, it is possible to use SMA available on the market. The silica powder used as a carrier should desirably have a high purity and a specific surface area of at least 500 $m^2/g$. If the specific surface area is smaller than 500 $m^2/g$, SMA is agglomerated on the surface of the silica carrier so as to inhibit the partial oxidation reaction of methane. The silica powder can be prepared by a known method. For example, a silica gel obtained by hydrolyzing ethyl silicate is dried and calcined to obtain a desired silica powder. A silica carrier having a desired specific surface area can be obtained by controlling the pH value in the hydrolyzing step. It should be noted that the pores present in the silica obtained by hydrolyzing ethyl silicate have an average diameter of about $40 \times 10^{-10}$ m. On the other hand, SMA molecules have an average diameter of about $28 \times 10^{-10}$ m. It follows that the SMA molecules can be held within the pores of the silica carrier even under a water vapor atmosphere described herein later, making it possible to suppress elution of the water-soluble SMA molecules so as to improve the durability of the catalyst. However, a silica powder available on the market can also be used satisfactorily in the present invention as the silica carrier.

It is desirable for SMA to be supported on the silica carrier in an amount of at least 10 mass %, preferably 10 to 50 mass %, and most preferably 25 to 40 mass %, based on the weight of the silica carrier. If the amount of SMA supported on the carrier is less than 10 mass %, the methane conversion rate is low, resulting in failure to obtain formaldehyde at a sufficiently high yield. If the supported SMA amount exceeds 50 mass %, however, it is impossible to obtain formaldehyde at a high yield conforming with the supported SMA amount. It should be noted in this connection that a regeneration reaction of SMA given below, which will be described herein later, takes place under a water vapor atmosphere:

What should be noted is that the SMA formation amount by the regeneration reaction given above is limited to a certain value. As a result, formaldehyde cannot be obtained at a high yield conforming with the SMA amount where the amount of SMA supported on the carrier exceeds 50 mass %, as pointed out above. Incidentally, the amount of SMA supported on the carrier can be controlled as desired by controlling the SMA concentration in the aqueous solution of SMA in the catalyst preparation method described above.

For producing formaldehyde in the present invention, a mixed gas of methane and oxygen is brought into contact with the catalyst of the present invention. For example, a mixed gas of methane and oxygen is passed through a bed of the catalyst of the present invention, which is heated to a predetermined temperature, so as to carry out reaction between methane and oxygen.

As already described, the novel catalyst of the present invention is a silica-supported SMA catalyst consisting of SMA supported on silica. The catalyst of the present invention is poor in thermal stability. If heated to the reaction temperature, e.g., 600° C., the catalyst tends to be thermally decomposed. Therefore, in the method of the present invention for producing formaldehyde, it is desirable to develop a technique that permits elevating the temperature of the silica-supported SMA catalyst to the reaction temperature while suppressing the thermal decomposition of the silica-supported SMA catalyst in order to enable the catalyst to exhibit sufficiently the catalytic function inherent in SMA. Under the circumstances, a very interesting technique has been developed by the present inventors as follows.

In the present invention, it is desirable to supply water vapor to a mixed gas of methane and oxygen so as to carry out the synthetic reaction of formaldehyde under a water vapor atmosphere. The reason for the requirement of the water vapor atmosphere is as follows.

In general, SMA is poor in heat resistance. If heated to temperatures not lower than 350° C., SMA is readily decomposed thermally to form silica and molybdenum oxide. If SMA is supported on silica, the heat resistance is improved. However, if heated to the synthesizing temperature of formaldehyde employed in the method of the present invention, preferably 550 to 650° C. as described herein later, SMA is thermally decomposed substantially completely into silica and molybdenum oxide. However, if water vapor is present in a sufficiently large amount in the reaction atmosphere, SMA is regenerated as denoted by reaction formula (I) given below, with the result that the thermal decomposition and regeneration of SMA proceed in equilibrium to cause SMA to be kept present in the reaction system:

In other words, the presence of the water vapor in the reaction system serves to suppress the thermal decomposition of SMA so as to enable SMA to exhibit the catalytic function inherent in SMA.

The present inventors have also conducted an extensive research with attentions paid to the temperature elevation rate of the SMA catalyst, finding a very interesting relationship between the decomposition-regeneration of SMA and the temperature elevation rate under a water vapor atmosphere.

Specifically, it is desirable in the present invention to heat the silica-supported SMA catalyst to the reaction temperature at a temperature elevation rate not lower than 100° C./min. The reason for heating the catalyst at the particular temperature elevation rate is as follows.

Specifically, SMA is thermally decomposed as denoted by reaction formula (II) given below, as described in, for example, "H. Hu et al., J. Phys. Chem., 99, 10897 (1995)" and "C. R. Deltcheff et al., J. Catal., 125, 292 (1990)."

As denoted by reaction formula (II) given above, SMA is completely decomposed to molybdenum oxide ($\alpha$-MoO$_3$) under the synthetic reaction temperature of formaldehyde, e.g., 600° C. However, since SMA is regenerated under a water vapor atmosphere as denoted by reaction formula (I) given previously, the decomposition-regeneration of SMA is repeated so as to seemingly suppress decomposition of SMA. However, the reaction rate of the reaction denoted by formula (I) is greatly dependent on the size of the molybdenum oxide particles. Where the molybdenum oxide particles are very small, e.g., average particle diameter not larger than $20 \times 10^{-10}$ m, the reaction of formula (I) proceeds at a high reaction rate. If the molybdenum oxide particles are large, however, the reaction of formula (I) proceeds very slowly so as to impair regeneration of SMA.

What is important in this connection is the temperature elevation rate of the silica-supported SMA catalyst. If the temperature of the SMA catalyst is slowly elevated to reach the reaction temperature, the processes of the SMA decomposition shown in reaction formula (II) proceed substantially in equilibrium. As a result, growth of the decomposition intermediate formed in each process is promoted, leading to formation of the final decomposition product of molybdenum oxide in the form of crystals having a large particle diameter. However, if the temperature elevation rate is increased, the decomposition processes proceed in non-equilibrium and, thus, the particle growth is not promoted. As a result, the final decomposition product of molybdenum oxide is in the form of crystals having a small particle diameter. In this case, SMA can be regenerated easily under a water vapor atmosphere as denoted by reaction formula (I).

This finding is very important and is effectively utilized in the process of heating the SMA catalyst to the reaction temperature. Specifically, depending on the mode of elevating the temperature of the SMA catalyst, SMA is already converted into molybdenum oxide crystals having a large particle diameter at the stage of reaching the reaction temperature. In this case, it is difficult to regenerate SMA. Under the circumstances, in order to enable SMA to exhibit sufficiently the catalytic function inherent in SMA, it is desirable to heat the catalyst to the operating temperature at a temperature elevation rate not lower than a predetermined level. If the SMA catalyst is heated at a desired temperature elevation rate, molybdenum oxide is present in the form of ultra fine particles, preferably ultra fine particles having an average particle diameter not larger than $20 \times 10^{-10}$ m, at the stage of reaching a predetermined reaction temperature, making it possible to regenerate SMA easily in accordance with reaction formula (I). In the method of the present invention for producing formaldehyde, the temperature elevation rate in the presence of the silica-supported SMA catalyst should desirably be not lower than 100° C./min.

The reaction in the present invention proceeds satisfactorily if the volume ratio of methane/oxygen in the mixed gas falls within a range of between 9/1 and 4/6. However, in order to obtain formaldehyde efficiently in terms of the methane conversion rate and the formaldehyde selectivity, it is more desirable for the volume ratio of methane/oxygen in the mixed gas to fall within a range of between 7/3 and 6/4.

In the present invention, the reaction for synthesizing formaldehyde should desirably be carried out at 550 to 650° C. If the reaction temperature is lower than 550° C., the methane conversion rate is lowered, leading to a low formaldehyde yield. Also, if the reaction temperature is higher than 650° C., the selectivity of carbon dioxide or carbon monoxide is increased so as to lower the formaldehyde yield. More preferably, the reaction temperature should be 580 to 620° C. The reaction mechanism given below is considered to account for the reaction temperature specified in the present invention:

$$CH_4(g)+H^+(ad) \rightarrow CH_5^+(ad) \quad (1)$$

$$O_2(g)+2s \rightarrow 2O^-(ad) \quad (2)$$

$$CH_5^+(ad)+2O^-(ad) \rightarrow CH_3O^+ + H_2O(g)+2s \quad (3)$$

$$H_2O(g)+2s \rightarrow OH^-(ad)+H^+(ad) \quad (4)$$

$$CH_3O^+(ad)+OH^-(ad) \rightarrow HCHO(g)+H_2O(g)+2s \quad (5)$$

$$CH_3O(ad)+2.5O^-(ad) \rightarrow CO_2(g)+1.5H_2O(g)+3.5s \quad (6)$$

$$CH_3O(ad)+1.5O^-(ad) \rightarrow CO(g)+H_2O(g)+2.5s \quad (7)$$

In the reaction formulas given above, the mark "(ad)" represents an adsorbed state, and "s" denotes the active site on the SMA catalyst. Formaldehyde is formed by reactions (1) to (5). However, reactions (6) and (7) also take place to form carbon dioxide and carbon monoxide. Also, the mark "$H^+(ad)$" represents a proton present on SMA. A single SMA molecule has four protons. For synthesizing formaldehyde by partial oxidation of methane, it is absolutely necessary to form an adsorbed methoxy group "$CH_3O(ad)$". In the case of using a silica-supported SMA catalyst, it is a strong likelihood that a carbonium cation "$CH_5^+(ad)$" is formed first by the action of $H^+(ad)$ and, then, the carbonium cation $CH_5^+(ad)$ is converted into the adsorbed methoxy group $CH_3O(ad)$. Where the reaction temperature is low, the activation and adsorption of methane shown in reaction (1) does not proceed. On the other hand, where the reaction temperature is high, the side reactions (6) and (7) are promoted so as to inhibit formation of methanol or formaldehyde.

In the present invention, water vapor should be supplied in an amount of 40 to 80% by volume of the total volume of the mixed gas of methane and oxygen and the water vapor. Preferably, water vapor should be supplied in an amount of 60 to 70% by volume of the total volume in order to obtain formaldehyde efficiently in view of the methane conversion rate and the formaldehyde selectivity.

EXAMPLES

A novel catalyst excellent in partial oxidation activity of methane, which is prepared by having SMA supported on silica, and a method of producing formaldehyde in the presence of the particular catalyst will now be described with reference to Examples.

First of all, a method of preparing a silica powder used as a carrier of the catalyst will now be described as Preparation Example 1.

Preparation Example 1
Preparation of Silica Powder Used as a Carrier

A silica gel obtained by hydrolyzing ethyl silicate was dried at 110° C. for 10 hours, followed by calcining the dried silica gel at 600° C. for 3 hours so as to prepare a high purity silica used as a carrier for preparing a silica-supported SMA catalyst of the present invention. Three kinds of silica carriers differing from each other in the specific surface area as shown in Table 1 below were prepared by changing the pH value in the hydrolyzing step.

TABLE 1

Silica powders having different specific surface areas

|  | pH in hydrolyzing step | Specific surface area (m²/g) |
|---|---|---|
| Silica powder 1 | 1.0 | 390 |
| Silica powder 2 | 2.0 | 570 |
| Silica powder 3 | 2.5 | 740 |

Preparation of a silica-supported SMA catalyst will now be described as Example 1.

Example 1
Preparation of Silica-Supported SMA Catalyst

A silica-supported SMA catalyst was prepared by an impregnation method as follows.

In the first step, 5 g of an SMA powder available on the market was dissolved sufficiently in 50 milliliters (mL) of pure water at room temperature, followed by transferring the resultant SMA solution into an evaporating dish and subsequently dipping 20 g of the silica powder prepared in Preparation Example 1 in the SMA solution. Then, the silica-containing solution was heated at about 50° C. above a water bath while stirring the solution to evaporate water such that the catalyst was not dried completely. The catalyst having water evaporated therefrom was put in a dryer kept at about 110° C. for further drying for 10 hours. The resultant catalyst, which was found to contain 20 mass % of SMA supported on the silica carrier, was put in a hermetically sealed polyethylene bag and stored in a desiccator.

A method of evaluating the activity of the silica-supported SMA catalyst prepared in Example 1 and a reaction apparatus for evaluating the activity by the particular method will now be described as Example 2.

Figure 1:
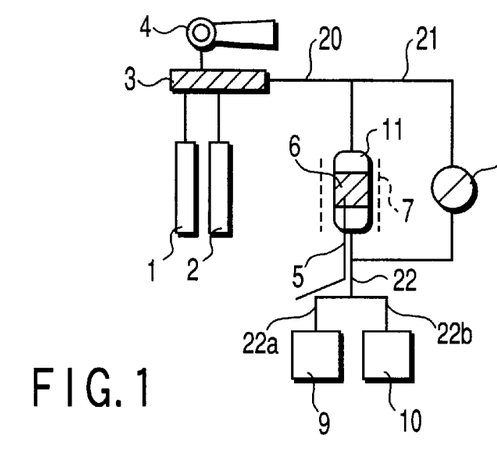
FIG. 1 schematically shows an apparatus for evaluating the activity of a silica-supported 12-molybdosilicic acid (SMA) catalyst.

Example 2
Method of Evaluating Activity of Silica-Supported SMA Catalyst and Reaction Apparatus for Activity Evaluation FIG. 1 schematically shows a reaction apparatus for evaluating the activity of the silica-supported SMA catalyst of the present invention. As shown in the drawing, a methane bomb 1, an oxygen bomb 2 and a water supply device 4 are connected to a gas mixer 3 through pipes. Also, the gas mixer 3 is connected to a reaction tube 11 through a pipe 20. The pipe 20 is branched upstream of the reaction tube 11, and a branched pipe 21 connected at one end to the branched portion of the pipe 20 communicates at the other end with a valve 8. A pipe 22 communicates at one end with the outlet port of the reaction tube 11 and is connected at the other end to gas chromatographs 9 and 10 through branched pipes 22a, 22b, respectively. The branched pipe 21 communicates with the pipe 22 via the valve 8. A catalyst 6 is loaded in the reaction tube 11, and a heater 7 is arranged to surround the reaction tube 11. Further, a thermocouple 5 is inserted into the reaction tube 11.

Methane and oxygen are supplied from the bombs 1 and 2 into the gas mixer 3 at supply rates of, generally, 1.8 L (liters)/h and 0.2 L/h, respectively. The water supplied from the water supply device 4 is converted into water vapor within the gas mixer 3 heated to 250° C. The water vapor is mixed completely before entering the catalyst layer with the methane and oxygen by the action of ceramic pieces (not shown) such as glass beads (5 mmφ) loaded in the mixer 3. In order to prevent occurrence of a pulsating flow of water during the reaction, a press fitting device for a liquid chromatography is used as the water supply device 4. The water vapor supply rate can be controlled freely within a range of between 0.2 L/h and 4 L/h.

The mixed gas is supplied into the gas chromatographs 9 and 10 through the branched pipes 22a and 22b, respectively. Carbosieve S-II is loaded in the column of the gas chromatograph 9 for measuring mainly methane, carbon monoxide and carbon dioxide. On the other hand, APS-201 is loaded in the column of the gas chromatograph 10 for measuring mainly methanol, formaldehyde and water. If the valve 8 mounted to the branched pipe 21 is closed, the mixed gas is introduced into the reaction tube 11 having a diameter of 10 mm and loaded with 1.5 g of the catalyst 6. The catalyst layer 6 is heated at a heating rate of between 100 and 150° C./min by the heater 7 set at 550 to 650° C., and the temperature within the reaction tube 11 is measured by the thermocouple 5. The formed gas passing through the catalyst layer 6 is also introduced into the gas chromatographs 9 and 10 for the composition analysis like the mixed gas flowing through the branched pipe 21. The main component of the formed gas is formaldehyde. However, about 5% by mass of methanol based on the amount of formaldehyde is also contained in the formed gas. Therefore, formaldehyde and methanol are denoted together by the expression "methanol/formaldehyde" in the following description.

The activity of the catalyst was evaluated by calculating the methane conversion rate and the selectivity of each of methanol/formaldehyde, carbon dioxide and carbon monoxide within the formed gas by the formulas given below:

Methane Conversion Rate=P/the number of moles of introduced methane;

Selectivity of Formed Compound X=the number of moles of formed compound X/P where P denotes the total number of moles of (methanol/formaldehyde+CO+$CO_2$), and X denotes the number of moles of methanol/formaldehyde, CO or $CO_2$.

The influences given by the water vapor addition amount to the activity of the silica-supported SMA catalyst will now be described as Example 3.

Example 3

Dependence of Catalyst Activity on Water Vapor Addition Amount

Figure 2:
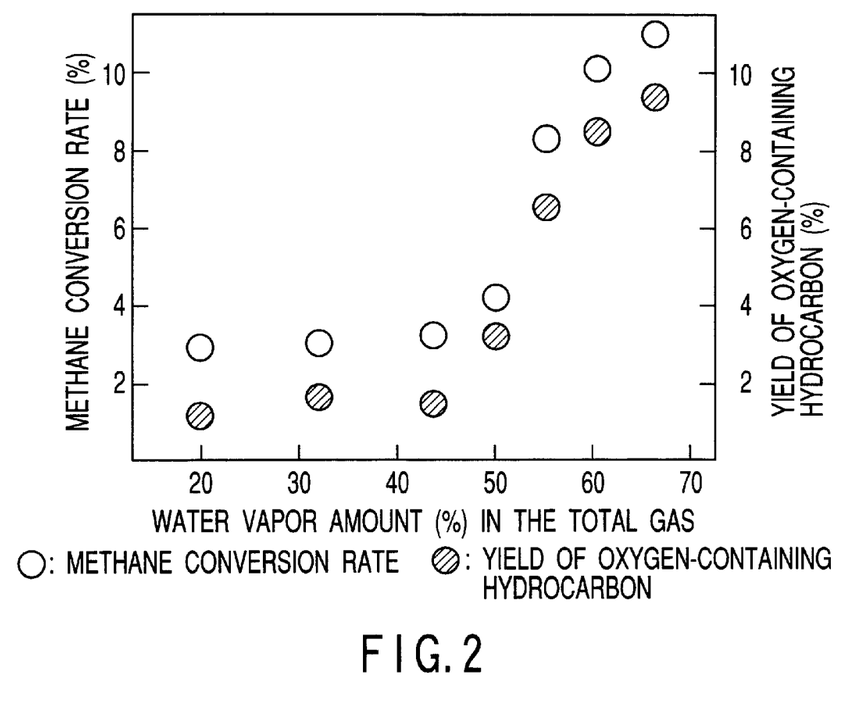
FIG. 2 is a graph showing the relationship between the catalytic activity and the water vapor supply amount.

A catalyst having 27 mass % of SMA supported on the silica powder 2 prepared in Preparation Example 1 was prepared as in Example 1. The catalyst thus prepared is abbreviated herein as "27mass %SMA/$SiO_2$". The catalytic activity was evaluated by the method of Example 2. Specifically, the methane conversion rate and the selectivity of each of methanol/formaldehyde, CO and $CO_2$ were calculated under the conditions given below:

Catalyst loading amount: 1.5 g
Methane flow rate: 1.8 L/h
Oxygen flow rate: 0.2 L/h
Reaction temperature: 600° C.
Heating rate to reaction temperature: 100 ° C./min
Water vapor addition rate: 0.5 L/h to 3.5 L/h The yield of methanol/formaldehyde was also calculated based on the calculated values of the methane conversion rate and the selectivity. The results are shown in Table 2 and in FIG. 2.

TABLE 2

Change in catalytic activity caused by change in water vapor addition amount

| | | | | | | | |
|---|---|---|---|---|---|---|---|
| Water vapor addition rate (L/h) | 0.5 | 1.0 | 1.5 | 2.0 | 2.5 | 3.0 | 3.5 |
| Water vapor partial pressure in total gas (%) | 20 | 33 | 43 | 50 | 56 | 60 | 64 |
| Methane conversion rate (%) | 3.0 | 3.0 | 3.1 | 4.0 | 8.4 | 10.5 | 11.3 |
| Methanol/formaldehyde selectivity (%) | 37.1 | 59.0 | 45.3 | 67.2 | 77.5 | 81.0 | 83.9 |
| Co selec-tivity (%) | 24.2 | 20.3 | 22.5 | 12.4 | 4.7 | 9.1 | 7.8 |
| $CO_2$ selec-tivity (%) | 38.7 | 20.7 | 32.2 | 20.3 | 17.8 | 9.9 | 9.0 |
| Methanol/formaldehyde yield (%) | 1.11 | 1.75 | 1.42 | 2.70 | 6.53 | 8.52 | 9.44 |

*27 mass % SMA/$SiO_2$, specific surface area of silica: 570 $m^2/g$
*Methane flow rate: 1.8 L/h, oxygen flow rate: 0.2 L/h
*Reaction temperature: 600° C., Heating rate: 100° C./min As apparent from the experimental data, the methane conversion rate, the methanol/formaldehyde selectivity and the methanol/formaldehyde yield are increased with increase in the water vapor amount within the total gas. Particularly, it has been confirmed that, if the water vapor partial pressure is increased to 60% or more, the methane conversion rate is rapidly increased and the methanol/formaldehyde selectivity is increased to exceed 80%, supporting that methane is efficiently converted into methanol/formaldehyde. It has also been confirmed that the methanol/formaldehyde yield exceeds 8%, which is markedly higher than 4% that was regarded as an unbreakable wall in this technical field. The amount of methanol in the methanol/formaldehyde was found to be not larger than 5 mass % of the amount of formaldehyde under each of the water vapor partial pressures tested. This was also the case with any of the following Examples.

As described above, it has been found that the water vapor addition to the methane/oxygen mixed gas is highly effective for improving the formaldehyde field, and that the effect produced by the water vapor addition is prominently increased if the water vapor partial pressure is 60% or more. In order to clarify the role played by the water vapor for improving the catalytic function, the structure of the SMA catalyst in the presence of water vapor was studied by an infrared spectroscopic analysis in Example 4 that follows.

Example 4

Role Played by Water Vapor for Improving Catalytic Function

Figure 3:
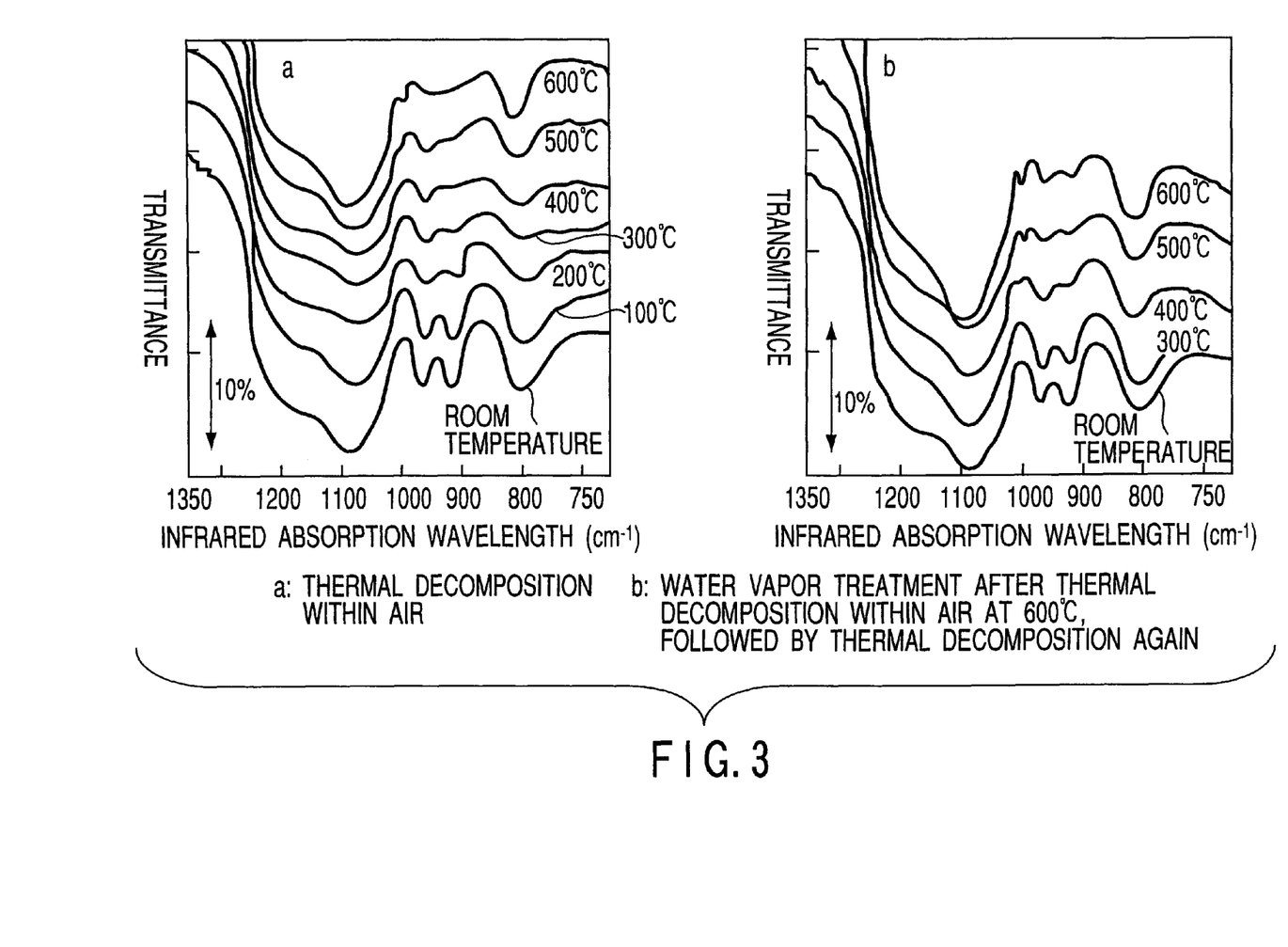
FIG. 3 shows an infrared spectrum denoting the thermal decomposition behavior of a 27 mass % $SMA/SiO_2$ catalyst.

The catalyst used in Example 3, i.e., 27 mass %SMA/$SiO_2$, was diluted with a KBr powder to form a pellet sample for the IR spectroscopic analysis. The pellet sample thus formed was put in a heating type infrared spectroscopic cell for measuring the infrared absorption spectrum. In example 4, the reaction was carried out under the heating rate to reaction temperature of 100° C./min. FIG. 3a shows the changes in the infrared absorption spectra when the pellet sample was heated under the air atmosphere. The measurements were carried out at room temperature after cooling the samples down to room temperature. Two absorption peaks observed at 907 $cm^{-1}$ and 954 $cm^{-1}$ are inherent in SMA. If the pellet sample is heated to 400° C. or more, these two peak intensities are attenuated and a single absorption peak is newly observed at 1000 cm$^{-1}$. The new absorption peak is characteristic of molybdenum oxide ($MoO_3$). If the sample is heated to 600° C., the absorption peaks ascribed to SMA disappear substantially completely, and only the absorption peak ascribed to $MoO_3$ can be observed.

In general, SMA is poor in heat resistance. If heated to 350° C. or higher, SMA is easily decomposed to form silica and molybdenum oxide as given below:

$$H_4SiMo_{12}O_{40} \rightarrow SiO_2 + 12MoO_3 + 2H_2O$$

On the other hand, the experimental data given in FIG. 3a suggest that the heat resistance of SMA may be improved if SMA is supported on silica. Even in this case, SMA is thermally decomposed substantially completely into silica and molybdenum oxide if heated at 600° C.

The sample thermally decomposed completely was cooled to room temperature and left to stand under a water vapor atmosphere for 12 hours, followed by observing the absorption spectra. FIG. 3b shows the results. In this case, two absorption peaks were observed at 907 cm$^{-1}$ and 954 cm$^{-1}$, and an absorption peak was not observed at 1000 cm$^{-1}$. This suggests that SMA was gradually regenerated by the treatment with water vapor. Incidentally, it is known to the art that a small amount of SMA is formed if a silica powder and a molybdenum oxide powder are mixed and stirred within water, as described in, for example, "J. M. Tatibouet, et al., J. Chem. Soc., Chem. Commun., 1260 (1988)" and "C. R. Deltcheff, et al., J. Catal., 125, 292 (1990)":

$$SiO_2 + 12MoO_3 + 2H_2O \rightarrow H_4SiMo_{12}O_{40} \quad (I)$$

If heated, the regenerated SMA begins to be thermally decomposed at 400° C. and is thermally decomposed completely at 600° C. to form silica and molybdenum oxide, as in FIG. 3a.

What should be noted is that, under the water vapor atmosphere, the thermal decomposition and regeneration of SMA proceed in equilibrium, with the result that SMA is constantly present during the reaction. In other words, the presence of water vapor serves to suppress decomposition of SMA during the reaction. Under the circumstances, water vapor is considered to regenerate SMA during the reaction so as to permit SMA to produce a catalytic function inherent in SMA.

The influences given by the supported amount of SMA to the catalytic activity will now be described as Example 5.

Example 5

Dependence of Catalytic Activity on Supported Amount of SMA

Figure 4:
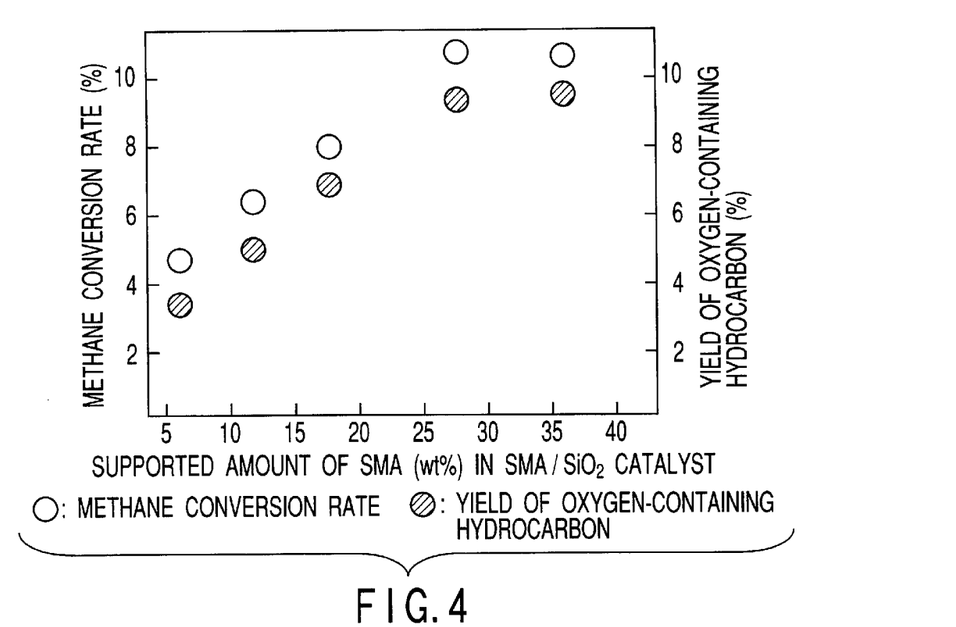
FIG. 4 is a graph showing the relationship between the catalytic activity and the amount of SMA supported on the carrier.

It has been confirmed in Example 3 that the yield of methanol/formaldehyde is markedly increased where the water vapor supply rate is set at 3.0 to 3.5 L/h (water vapor partial pressure of 60 to 64%). In Example 5, an experiment was conducted under a water vapor supply rate of 3.5 L/h by changing the amount of SMA supported on silica powder 2 in order to observe the change in the catalytic activity caused by the change in the amount of the supported SMA. The other reacting conditions were equal to those in Example 3, as given below:

Methane flow rate: 1.8 L/h
oxygen flow rate: 0.2 L/h
Reaction temperature: 600° C.
Heating rate to reaction temperature: 100° C./min The amount of the supported SMA was changed within a range of 6 to 36 mass %. The experimental data are shown in Table 3 and FIG. 4.

TABLE 3

Change in catalytic activity caused by change in amount of supported SMA

| Amount of supported SMA (% by mass) | 6 | 12 | 18 | 27 | 36 |
|---|---|---|---|---|---|
| Methane conversion rate (%) | 4.3 | 6.5 | 7.9 | 11.3 | 11.0 |
| Methanol/formaldehyde selectivity (%) | 84.8 | 71.4 | 83.2 | 83.9 | 86.6 |
| CO selectivity (%) | 2.6 | 12.9 | 3.6 | 7.8 | 4.8 |
| $CO_2$ selectivity (%) | 12.6 | 15.7 | 13.2 | 9.0 | 8.5 |
| Methanol/formaldehyde yield (%) | 3.67 | 4.66 | 6.60 | 9.44 | 9.56 |

Specific surface area of silica: 570 m$^2$/g
Methane/oxygen/water vapor flow rate (L/h): 1.8/0.2/3.5
Reaction temperature: 600° C.,
Heating rate: 100° C./min The experimental data indicate that the methane conversion rate is increased with increase in the supported amount of SMA, leading to an increased yield of methanol/formaldehyde, though the selectivity of methanol/formaldehyde is not appreciably changed by the change in the supported amount of SMA. Particularly, a prominently high yield of methanol/formaldehyde, i.e., about 10%, was obtained where the supported amount of SMA exceeded 18 mass %.

The influences given by the methane/oxygen ratio of the methane/oxygen mixed gas to the catalytic activity will now be described as Example 6.

Example 6

Dependence of Catalytic Activity on Methane/Oxygen Ratio

The direct synthesis of formaldehyde by partial oxidation of methane proceeds as follows:

$$CH_4 + O_2 \rightarrow HCHO + H_2O$$

Figure 5:
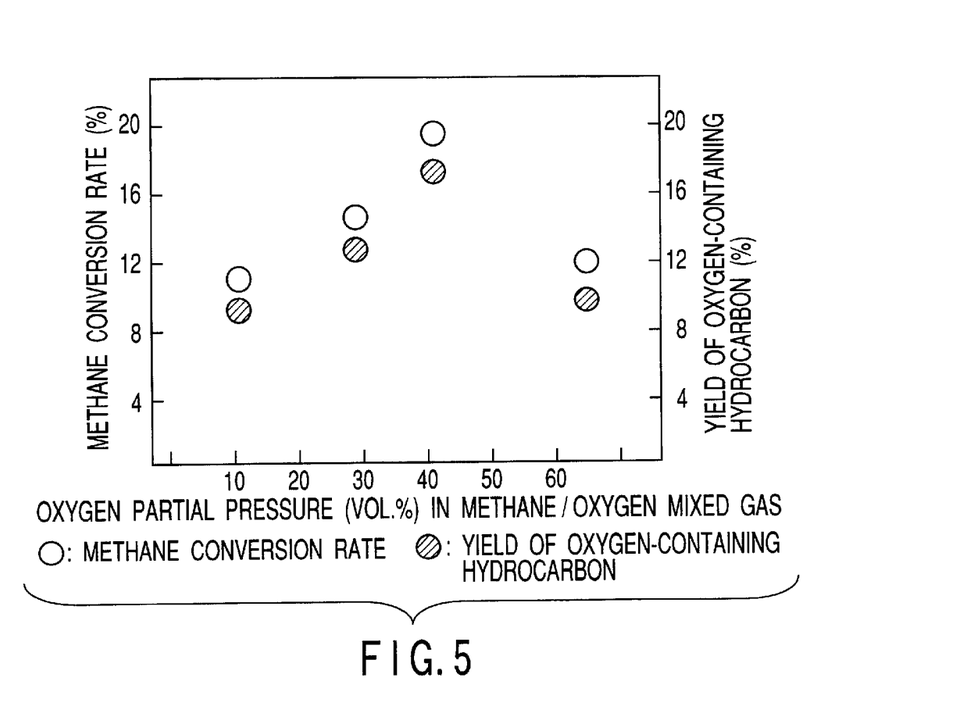
FIG. 5 is a graph showing the relationship between the catalytic activity and methane/oxygen volume ratio.

Clearly, it is stoichiometrically desirable for the methane/oxygen ratio of the methane/oxygen mixed gas used in the reaction to be 1/1. In each of the experiments conducted in the Examples described above, the methane/oxygen ratio was set at 9/1. In Example 6, 1.5 g of 27mass % SMA/$SiO_2$ catalyst was used, and the reaction was carried out under a water vapor flow rate of 3.5 L/hr, the reaction temperature of 600° C. and the heating rate to the reaction temperature of 100° C./min, while changing the methane/oxygen ratio within a range of 9/1 to 4/6 for evaluating the catalytic activity. On the other hand, the flow rate of the methane/oxygen mixed gas was set constant at 2.0 L/h. The experimental data are shown in Table 4 and FIG. 5.

TABLE 4

Change in catalytic activity caused by change in methane/oxygen ratio

| Methane/oxygen volume ratio | 9/1 | 7/3 | 6/4 | 4/6 |
|---|---|---|---|---|
| Methane conversion rate (%) | 11.3 | 13.9 | 19.7 | 12.2 |
| Methanol/formaldehyde selectivity (%) | 83.9 | 88.1 | 87.6 | 84.1 |

TABLE 4-continued

Change in catalytic activity caused by change in methane/oxygen ratio

| Methane/oxygen volume ratio | 9/1 | 7/3 | 6/4 | 4/6 |
|---|---|---|---|---|
| CO selectivity (%) | 7.8 | 5.0 | 6.2 | 5.1 |
| $CO_2$ selectivity (%) | 9.0 | 7.0 | 6.2 | 10.8 |
| Methanol/formaldehyde yield (%) | 9.44 | 12.25 | 17.25 | 10.22 |

Sum of methane/oxygen: 2.0 L/h
Water vapor flow rate: 3.5 L/h (water vapor partial pressure: 64%)
Amount of supported SMA(mass %): 27 mass %
Reaction temperature: 600 ° C.,
Heating rate: 100° C./min As shown in Table 4, the methane/oxygen volume ratio was changed stepwise from 9/1 to 4/6. In other words, the oxygen content of the methane/oxygen mixture was increased stepwise. The methanol/formaldehyde yield was found to increase with increase in the oxygen content of the methane/oxygen mixture to reach 17.25% when the methane/oxygen volume ratio was set at 6/4. Where the methane/oxygen volume ratio was held within a range of between 9/1 and 6/4, the methanol/formaldehyde selectivity of the reaction mixture was held substantially constant at 85% or more. Also, the selectivity of any of carbon monoxide and carbon dioxide was lower than 10%. Where the methane/oxygen volume ratio was set at 4/6, the methane conversion rate was decreased and the selectivity of the carbon dioxide was increased. As a result, the yield of methanol/formaldehyde was also lowered, though the methanol/formaldehyde yield was very high even in this case, i.e., 10.22%.

The effect given to the catalytic activity by the specific surface area of the silica carrier used in the production of the silica-supported SMA catalyst will now be described as Example 7.

Example 7

Dependence of Catalytic Activity on Specific Surface Area of Silica Carrier

A single SMA molecule has a diameter of about $28 \times 10^{-10}$ m and, thus, has a cross sectional area of about $600 \times 10^{-20}$ $m^2$. Also, SMA has a molecular weight of about 1824. Therefore, in the 27mass % SMA/SiO2 catalyst, 0.27 g of SMA, i.e., $0.9 \times 10^{20}$ SMA molecules, are supported by lg of silica. It should be noted that the sum of the cross sectional areas of $0.9 \times 10^{20}$ SMA molecules is 540 $m^2$. On the other hand, silica powder 2 shown in Table 1 was used as a silica carrier. As shown in Table 1, silica powder 2 has a specific surface area of 570 $m^2$/g. It follows that, in the 27 mass %SMA/SiO$_2$ catalyst, the entire surface of the silica carrier is covered substantially completely with a monolayer of the SMA molecules. In other words, if a larger amount of SMA molecules are supported on the silica carrier, the SMA molecules are caused to form a plurality of layers on the silica surface. According to the experimental data obtained in Example 5, the methanol/formaldehyde yield remains substantially constant if the amount of SMA supported on the carrier is 27 mass % or more. In other words, it is suggested that the catalytic activity substantially reaches saturation if SMA is supported in an amount sufficient to form a monolayer covering the entire surface of the silica carrier.

Figure 6:
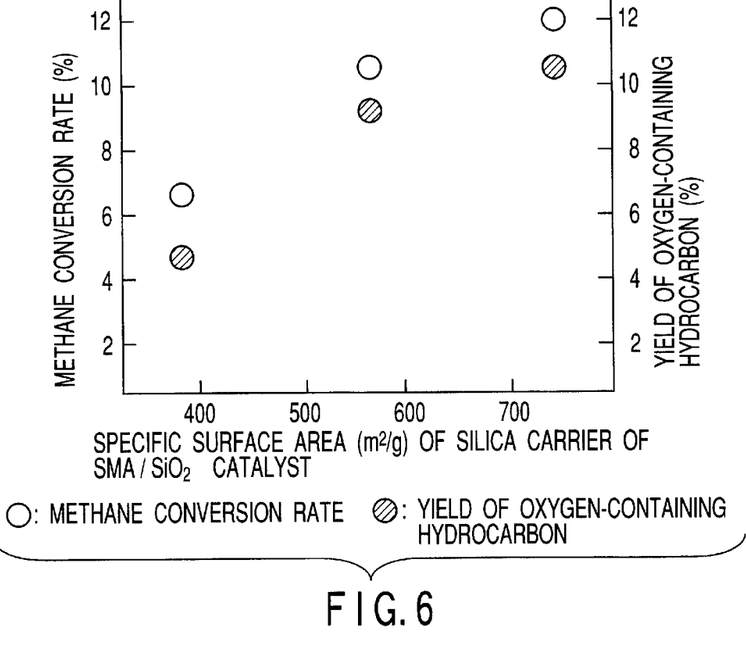
FIG. 6 is a graph showing the relationship between the catalytic activity and the specific surface area of silica used as a carrier.

In Example 7, a 27 mass % SMA/SiO$_2$ catalyst was prepared as in Example 1 by using each of silica powders 1, 2 and 3 prepared in Preparation Example 1, the silica powders differing from each other in specific surface area, for evaluating the catalytic activity. The reaction was carried out under the methane/oxygen ratio of the mixed gas of 9/1, the water vapor flow rate of 3.5 L/h, the reaction temperature of 600° C., and the heating rate to the reaction temperature of 100° C./min. Table 5 and FIG. 6 show the results.

TABLE 5

Change in catalytic activity caused by change in specific surface area of silica

| Specific surface area of SiO$_2$ ($m^2$/g) | 390 (Silica powder 1) | 570 (Silica powder 2) | 740 (Silica powder 3) |
|---|---|---|---|
| Methane conversion rate (%) | 6.4 | 11.3 | 12.1 |
| Methanol/formaldehyde selectivity (%) | 73.0 | 83.9 | 85.3 |
| CO selectivity (%) | 7.4 | 7.8 | 6.3 |
| $CO_2$ selectivity (%) | 19.6 | 9.0 | 8.3 |
| Methanol/formaldehyde yield (%) | 4.69 | 9.44 | 10.36 |

27 mass%SMA/SiO$_2$
Methane/oxygen/water vapor flow rate (L/h): 1.8/0.2/3.5
Reaction temperature: 6000° C., Heating rate: 100° C./min As apparent from the experimental data, silica powder 1 having the smallest specific surface area led to a low methane conversion rate and to a low selectivity of methanol/formaldehyde. As a result, the yield of methanol/formaldehyde for silica powder 1 was lower than those for the other silica powders. It is considered reasonable to understand that, in the catalyst prepared by using silica powder 1, SMA molecules are agglomerated on the surface of the silica carrier. This clearly suggests that the SMA agglomeration is not desirable for the partial oxidation of methane.

The reactions were carried out at 600° C. in Examples 3, 5, 6 and 7. Then, the effect given by the reaction temperature to the catalytic activity will now be described as Example 8.

Example 8

Dependence of Catalytic Activity on Reaction temperature

Figure 7:
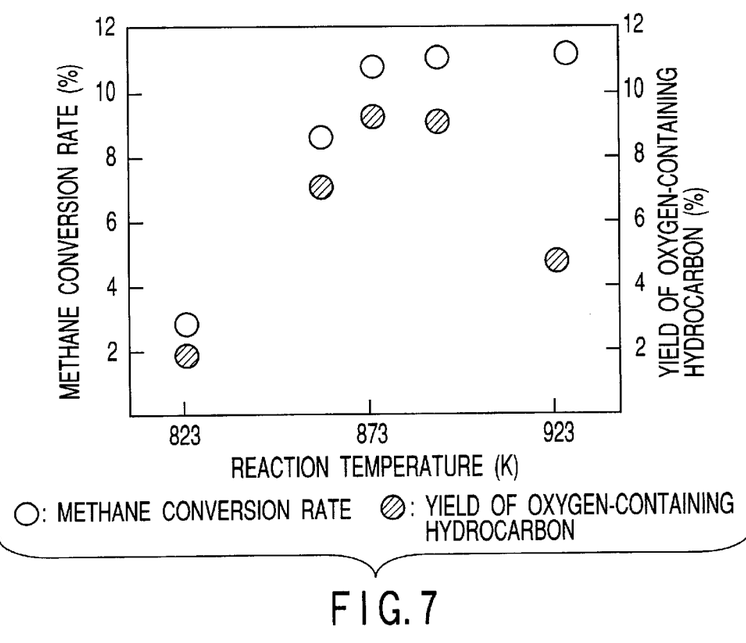
FIG. 7 is a graph showing the relationship between the catalytic activity and the reaction temperature.

The reaction was carried out under the conditions similar to those for Example 7. In Example 8, used was 1.5 g of a 27 mass % SMA/SiO$_2$ catalyst prepared by using silica powder 2, and the reaction temperature was changed within a range of between 550C and 650° C. (heating rate of 100° C./min) so as to evaluate the effect given by the reaction temperature to the catalytic activity. Table 6 and FIG. 7 show the results.

TABLE 6

Change in catalytic activity caused by change in reaction temperature

| Reaction temperature (° C.) | 550 | 580 | 600 | 620 | 650 |
|---|---|---|---|---|---|
| Methane conversion rate (%) | 2.7 | 8.6 | 11.3 | 11.5 | 11.8 |
| Methanol/formaldehyde selectivity (%) | 77.4 | 84.1 | 83.9 | 79.4 | 39.2 |
| CO selectivity (%) | 16.8 | 10.5 | 7.8 | 7.5 | 21.3 |
| $CO_2$ selectivity (%) | 5.8 | 5.4 | 9.0 | 13.1 | 39.5 |
| Methanol/formaldehyde yield (%) | 2.09 | 7.23 | 9.44 | 9.13 | 4.62 |

27 mass % SMA/SiO$_2$, specific surface area of silica: 570 $m^2$/g

Methane/oxygen/water vapor flow rate (L/h): 1.8/0.2/3.5

Heating rate: 100° C./min

The experimental data clearly support that the reaction of the present invention for synthesizing formaldehyde proceeds satisfactorily under the reaction temperatures of 550° C. to 650° C. Particularly, where the reaction temperature fell within a range of between 580° C. and 620° C., each of the methane conversion rate and the methanol/formaldehyde selectivity was found to be high, making it possible to obtain methanol/formaldehyde at a high yield.

The durability of the catalyst will now be described as Example 9.

Example 9
Durability of Silica-Supported SMA Catalyst

Figure 8:
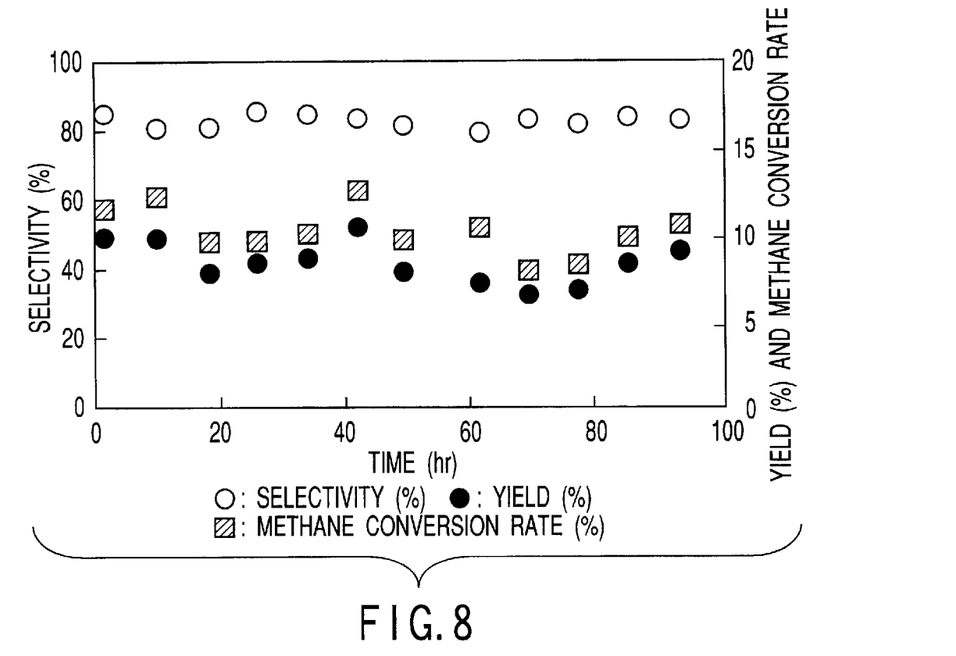
FIG. 8 is a graph showing the durability of the catalyst with 9/1 of methane/oxygen ratio.

Durability tests were conducted under different conditions by using 1.5 g of a 27 mass % $SMA/SiO_2$ catalyst. Specifically, one of the tests was conducted for 85 hours under the methane flow rate of 1.8 L/h, the oxygen flow rate of 0.2 L/h, the water vapor flow rate of 3.5 L/h, the reaction temperature of 600° C. and the heating rate to the reaction temperature of 100° C./min. Table 7 and FIG. 8 show the results.

TABLE 7

Durability test using 27 mass % $SMA/SiO_2$ catalyst

| Reaction time (h) | 1 | 17 | 33 | 49 | 61 | 85 |
|---|---|---|---|---|---|---|
| Methane conversion rate (%) | 11.3 | 9.3 | 9.9 | 9.5 | 8.9 | 9.8 |
| Methanol/formaldehyde selectivity (%) | 83.5 | 83.2 | 84.6 | 82.1 | 87.6 | 85.2 |
| Methanol/formaldehyde yield (%) | 9.44 | 7.52 | 8.36 | 7.77 | 7.17 | 8.39 |

27 mass % $SMA/SiO_2$

Specific surface area of silica: 570 $m^2/g$

Methane/oxygen/water vapor flow rate (L/h): 1.8/0.2/3.5

Reaction temperature: 600° C.,

Heating rate: 100° C./min

Figure 9:
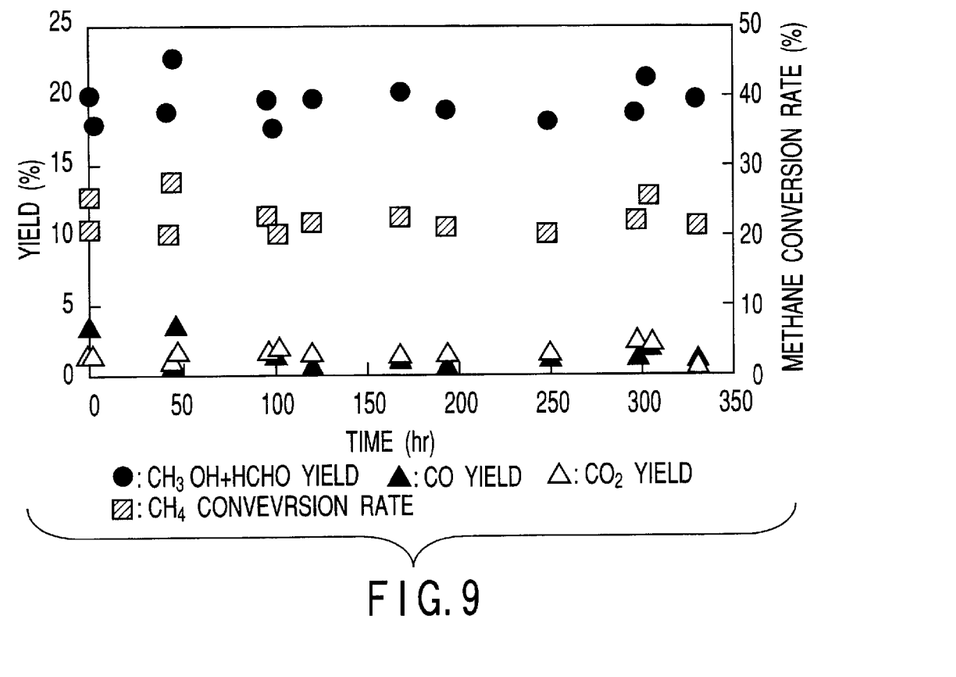
FIG. 9 is a graph showing the durability of the catalyst with 6/4 of methane/oxygen ratio.

The other test was conducted for 330 hours under the methane flow rate of 1.2 L/h, the oxygen flow rate of 0.8 L/h, the water vapor flow rate of 3.5 L/h and the reaction temperature of 600° C. and the heating rate to the reaction temperature of 100° C./min. Table 8 and FIG. 9 show the results.

TABLE 8

Durability test using 27 mass % $SMA/SiO_2$ catalyst

| Reaction time (h) | 1 | 43.2 | 100.4 | 193.3 | 250.0 | 330.0 |
|---|---|---|---|---|---|---|
| Methane conversion rate (%) | 25.2 | 20.0 | 20.1 | 20.5 | 19.6 | 24.5 |
| Methanol/formaldehyde selectivity (%) | 80.5 | 93.1 | 86.5 | 91.1 | 90.8 | 85.1 |
| Methanol/formaldehyde yield (%) | 20.28 | 18.58 | 17.41 | 18.67 | 17.77 | 20.87 |
| Material balance (%) | 109.5 | 91.0 | 110.3 | 98.9 | 103.6 | 104.3 |

27 mass% $SMA/SiO_2$

Specific surface area of silica: 50 $m^2/g$

Methane/oxygen/water vapor flow rate (L/H): 1.2/0.8/3.5

Reaction temperature: 600° C., Heating rate: 100° C./min

The experimental data clearly support that the catalyst of the present invention permits stably maintaining the methanol/formaldehyde yield over 330 hours. It has been found that, although SMA is soluble in water, SMA does not elute out of the catalyst layer even under the water vapor atmosphere so as to be held within the pores of the silica carrier, leading to an excellent durability of the catalyst.

The material balance of carbon, which has been determined by the formula given below, is also shown in Table 8:

Material Balance of Carbon=A/B×100 where A represents the sum of the unreacted methane, methanol, formaldehyde, CO and $CO_2$, and B denotes the amount of methane supplied to the reaction system.

The material balance fell within a range of between 90 and 110, supporting that the analysis was performed appropriately.

In each of the Examples described above, the heating rate to the reaction temperature was set at 100° C./min. The influences given by the heating rate to the catalytic activity will now be described as Examples 10 and 11.

Example 10
Relationship between Heating Rate and Effect of Suppressing Decomposition of Catalyst Loaded in a reaction tube having an inner diameter of 10 mm and made of quartz was 1.5 g of 27mas % $SMA/SiO_2$ catalyst. Then, 2.0 L/h of a methane/oxygen mixed gas (methane/oxygen volume ratio of 6/4) and 3.0 L/h of water vapor were introduced into the reaction tube. Temperature of the catalyst layer was elevated to 600° C. at a heating rate of each of 40° C./min, 60° C./min and 100° C./min and maintained at 600° C. for 15 minutes, followed by rapidly cooling the catalyst layer to room temperature. The water vapor supply was stopped at the time when the temperature of the catalyst layer was lowered to 300° C. during the rapid cooling process. The catalyst cooled to room temperature was taken out of the reaction tube so as to observe the state of decomposition of the $SMA/SiO_2$ catalyst by X-ray diffraction.

Figure 10:
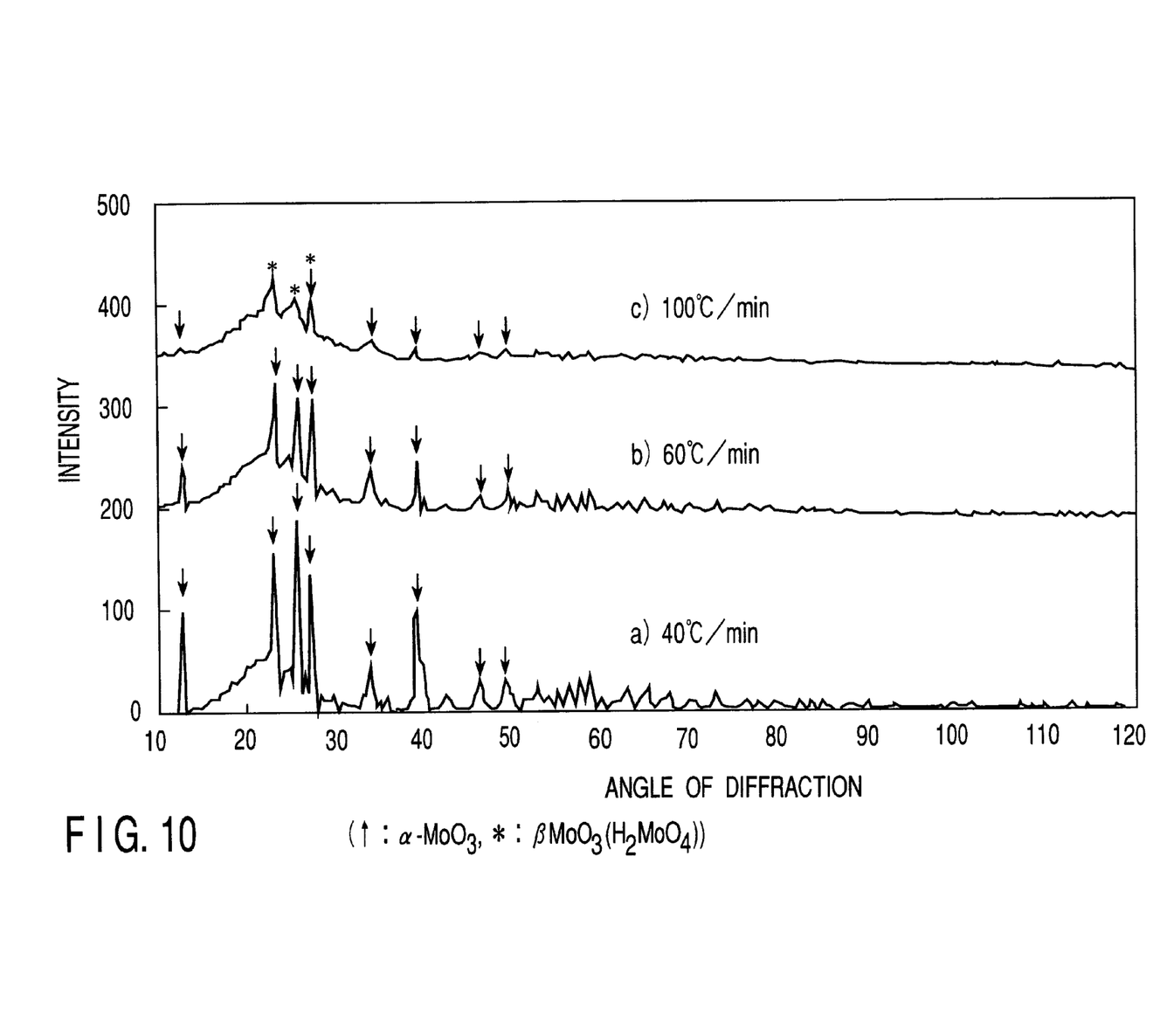
FIG. 10 shows the X-ray diffraction pattern of the catalyst heated to 600° C. at various temperature elevation rates.

FIG. 10 shows the X-ray diffraction pattern of the $SMA/SiO_2$ catalyst after the catalyst was heated to 600° C. at each of various heating rates. The arrows put in the diffraction pattern denote diffraction peaks characteristic of molybdenum oxide. These peaks clearly support that SMA was decomposed in the catalysts that were heated at relatively low heating rates of 40° C./min and 60° C./min so as to form large crystal grains of molybdenum oxide. On the other hand, the molybdenum oxide was formed in a small amount in the SMA catalyst that was heated rapidly at a heating rate of 100° C./min, suggesting that almost all portion of the SMA catalyst remained as it was. The diffraction peaks denoted by asterisks * in the diffraction pattern represent peaks belonging to β-molybdenum oxide ($MoO_3 \cdot H_2O$) formed by decomposition of SMA in the cooling process from 600° C. to room temperature.

As apparent from the experimental data, it is necessary to increase the heating rate in the process of heating the silica-supported SMA catalyst to the reaction temperature in order to suppress decomposition of the catalyst during the heating process. Preferably, it is desirable to heat the catalyst at a heating rate of at least 100° C./min.

Example 11

Dependence of Catalytic Activity on the Temperature Elevation Rate

Figure 11A:
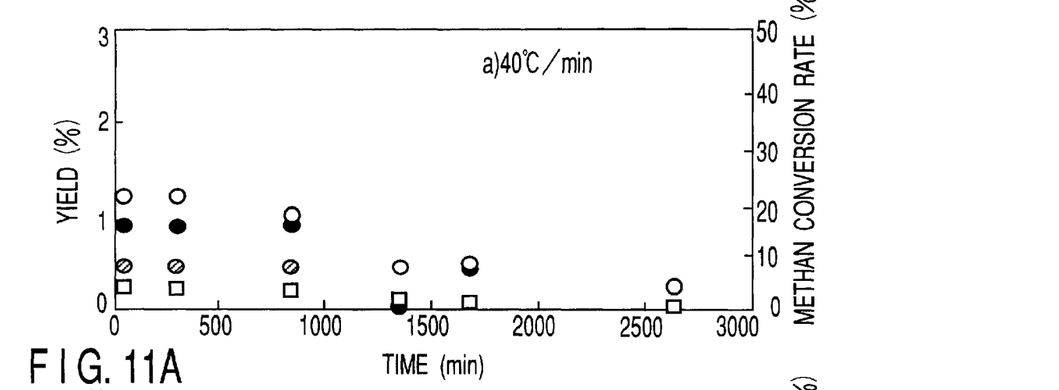
FIGS. 11A, 11B and 11C are graphs each showing the relationship between the catalytic activity and the temperature elevation rate.
Figure 11B:
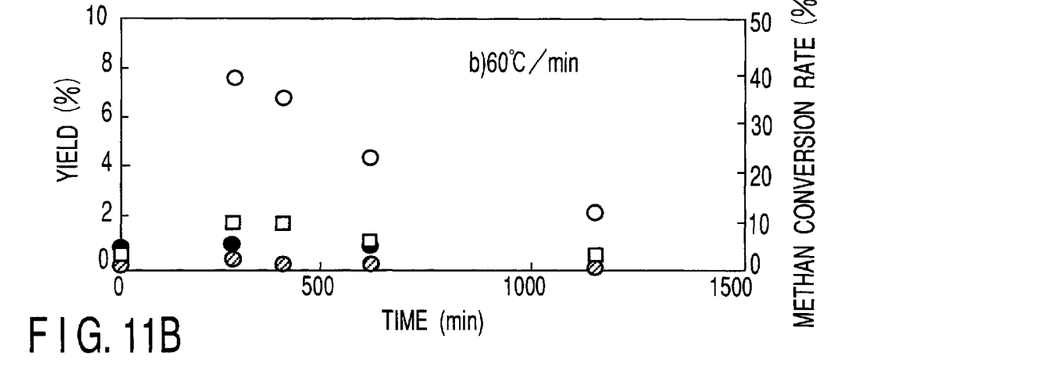
Figure 11C:
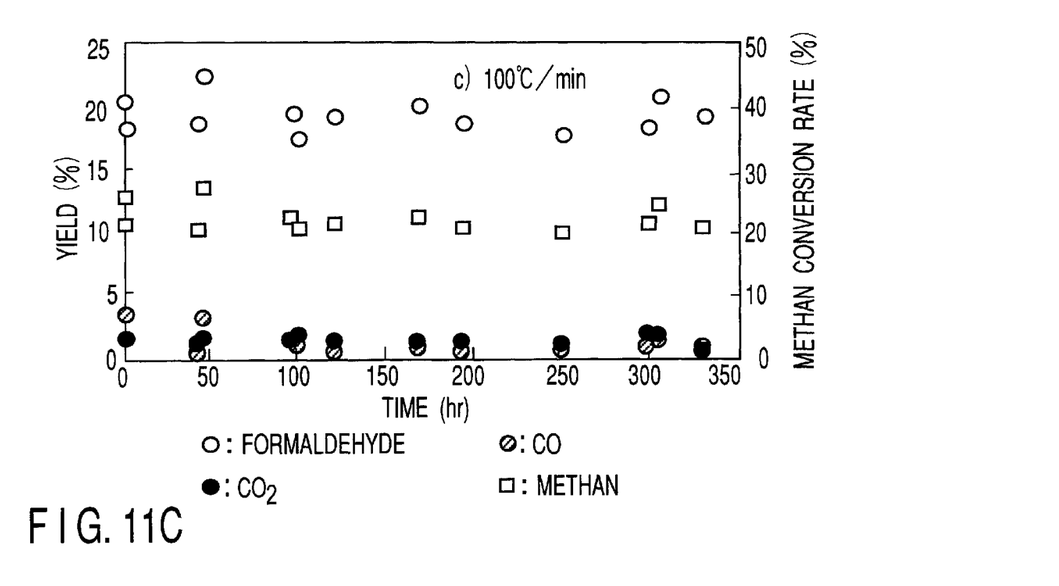

Loaded in a reaction tube having an inner diameter of 10 mm and made of stainless steel was 1.5 g of 27 mass % SMA/SiO$_2$ catalyst. Then, 2.0 L/h of a methane/oxygen mixed gas (methane/oxygen volume ratio of 6/4) and 3.0 L/h of water vapor were introduced into the reaction tube. Temperature of the catalyst layer was elevated to 600° C. at a heating rate of each of 40° C./min, 60° C./min and 100° C./min so as to initiate the partial oxidizing reaction of methane. The reaction mixture, which consisted of formaldehyde, carbon dioxide and carbon monoxide, was subjected to a quantitative analysis by means of a gas chromatography so as to evaluate the catalytic activity by the method equal to that employed in Example 2. Table 9 and FIG. 11 show the results.

TABLE 9

Relationship between heating rate and catalytic activity a) Heating rate of 40° C./min

| Reaction time (min) | 60 | 300 | 840 | 1350 | 1680 | 2640 |
|---|---|---|---|---|---|---|
| Methane conversion rate (%) | 2.6 | 2.6 | 2.4 | 0.9 | 0.9 | 0.5 |
| Formaldehyde selectivity (%) | 48.1 | 48.1 | 44.3 | 47.4 | 50.5 | 46.9 |
| Carbon dioxide selectivity (%) | 36.5 | 36.5 | 39.2 | 49.4 | 45.0 | 48.1 |
| Carbon monoxide selectivity (%) | 15.4 | 15.4 | 16.5 | 3.2 | 4.5 | 5.1 |
| Formaldehyde yield (%) | 1.24 | 1.24 | 1.06 | 0.41 | 0.47 | 0.24 | b) Heating rate of 60° C./min

| Reaction time (min) | 280 | 400 | 610 | 1150 | 1710 |
|---|---|---|---|---|---|
| Methane conversion rate (%) | 8.9 | 8.8 | 5.4 | 2.9 | 2.4 |
| Formaldehyde selectivity (%) | 86.0 | 77.7 | 81.3 | 79.8 | 69.6 |
| Carbon dioxide selectivity (%) | 9.9 | 20.6 | 16.0 | 17.9 | 26.3 |
| Carbon monoxide selectivity (%) | 4.2 | 1.7 | 2.7 | 2.2 | 4.2 |
| Formaldehyde yield (%) | 7.64 | 6.86 | 4.41 | 4.28 | 1.70 | c) Heating rate of 100° C./min

| Reaction time (min) | 1 | 43 | 100 | 193 | 250 | 330 |
|---|---|---|---|---|---|---|
| Methane conversion rate (%) | 25.2 | 20.0 | 20.1 | 20.5 | 19.6 | 24.5 |
| Formaldehyde selectivity (%) | 80.5 | 93.1 | 86.5 | 91.1 | 90.8 | 85.1 |
| Carbon dioxide selectivity (%) | 8.0 | 2.0 | 6.8 | 4.5 | 4.6 | 9.2 |
| Carbon monoxide selectivity (%) | 11.5 | 4.9 | 6.7 | 4.4 | 4.6 | 5.7 |
| Formaldehyde yield (%) | 20.3 | 18.6 | 17.4 | 18.7 | 17.8 | 20.9 |

As apparent from Table 9 and FIG. 11, the methane conversion rate was markedly low in the SMA/SiO$_2$ catalysts heated at the heating rates of 40° C./min and 60° C./min, compared with the catalyst heated at a heating rate of 100° C./min. This suggests that, since the active species of the reaction was SMA, SMA was decomposed in the catalysts heated at heating rates of 40° C./min and 60° C./min. Also, a large amount of the carbon dioxide gas was contained in the reaction mixture in the catalysts heated at heating rates of 40° C./min and 60° C./min. This implies that, since a carbon dioxide gas is generated in a large amount if the reaction is carried out in the presence of the silica-supported molybdenum oxide catalyst, SMA is decomposed to form molybdenum oxide in the case where the catalyst is heated at heating rates of 40° C./min and 60° C./min. As a result, it has been clarified that, in the case where the catalyst is slowly heated to the reaction temperature, SMA is decomposed into molybdenum oxide, leading to the result of reaction similar to that in the case of using a silica-supported molybdenum oxide catalyst.

On the other hand, where the SMA/SiO$_2$ catalyst is heated at a heating rate of 100° C./min, the catalyst maintained a high catalytic activity over 350 hours so as to achieve a methane conversion rate of about 20% and a formaldehyde selectivity of about 85%. Further, the carbon dioxide formation was only about 7%. These experimental data support that, if the silica-supported SMA catalyst is heated rapidly at a heating rate of 100/min, SMA is not decomposed during the heating. Even is SMA is decomposed to form molybdenum oxide, SMA is regenerated soon. It follows that the silica-supported SMA catalyst plays the role of the active species in the reaction of forming formaldehyde.

As pointed out above, the experimental data obtained in Example 9 clearly support that, if the silica-supported SMA catalyst is heated at such a high heating rate as 100° C./min or more, it is possible to suppress decomposition of the SMA catalyst in the heating step.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of producing formaldehyde in a system, comprising:
    conducting the reaction of methane and oxygen as a mixed gas in the presence of a catalyst consisting of 12-molybdosilicic acid supported on silica, in which 12-molybdosilicic acid is supported in an amount not less than 10 wt % on silica, the reaction being conducted in the presence of said catalyst in the system which is heated to the operating temperature at a rate not less than 100° C./min.

2. The method of producing formaldehyde according to claim 1, wherein the methane and oxygen gases are mixed by volume in a ratio of methane/oxygen ranging from 9/1 to 4/6, and the reaction temperature in the presence of said catalyst falls within a range of 550° C. to 650° C.

3. The method of producing formaldehyde according to claim 1, wherein water vapor is added to the mixed methane and oxygen gases in an amount of 40 to 80 % by volume based on the total reaction gas consisting of said mixed gas and said water vapor.

4. The method of producing formaldehyde according to claim 2, wherein water vapor is added to the mixed methane and oxygen gases in an amount of 40 to 80 % by volume based on the total reaction gas consisting of said mixed gas and said water vapor.

5. The method of producing formaldehyde according to claim 2, wherein the methane and oxygen gases are mixed by volume in a ratio of methane/oxygen ranging from 7/3 to 6/4, and the reaction temperature in the presence of said catalyst falls within a range of 580° C. to 620° C.

6. The method of producing formaldehyde according to claim 1, wherein the amount of 12-molybdosilicic acid supported on silica ranges from 10–50 wt %.

7. The method of producing formaldehyde according to claim 6, wherein the amount of 12-molybdosilicic acid supported on silica ranges from 25–40 wt %.

8. The method of producing formaldehyde according to claim 1, wherein the amount of 12-molybdosilicic acid supported on silica ranges from 10–50 wt %.

9. The method of producing formaldehyde according to claim 8, wherein the amount of 12-molybdosilicic acid supported on silica ranges from 25–40 wt %.

10. The method of producing formaldehyde according to claim 1, wherein the amount of 12-molybdosilicic acid supported on silica ranges from 10–50 wt %.

11. The method of producing formaldehyde according to claim 10, wherein the amount of 12-molybdosilicic acid supported on silica ranges from 25–40 wt %.

12. The method of producing formaldehyde according to claim 1, wherein the silica has a specific surface area not less than 500 $m^2/g$.

* * * * *